United States Patent [19]

Gutman

[11] 3,978,106

[45] Aug. 31, 1976

[54] CERTAIN THIOFORMALDOXIMINO DITHIOPHOSPHORIC ACIDS

[75] Inventor: Arnold D. Gutman, Berkeley, Calif.

[73] Assignee: Stauffer Chemical Company, Westport, Conn.

[22] Filed: Nov. 22, 1971

[21] Appl. No.: 201,190

Related U.S. Application Data

[62] Division of Ser. No. 26,149, April 6, 1970, Pat. No. 3,652,736.

[52] U.S. Cl. ............................ 260/453 R; 424/298; 260/465.5 R
[51] Int. Cl.[2] ....................................... C07C 119/18
[58] Field of Search ......... 260/453 R, 566 AE, 940, 260/981

[56] References Cited
UNITED STATES PATENTS

| | | | |
|---|---|---|---|
| 3,155,708 | 11/1964 | Chupp et al. | 260/981 |
| 3,419,620 | 12/1968 | Becher et al. | 71/87 |
| 3,536,789 | 10/1970 | Lorenz | 260/940 |
| 3,551,529 | 12/1970 | Kaugars | 260/566 AE |

FOREIGN PATENTS OR APPLICATIONS 710,649    8/1968    Belgium .......................... 260/453 R

*Primary Examiner*—Glennon H. Hollrah
*Attorney, Agent, or Firm*—Edwin H. Baker

[57] ABSTRACT

Compounds having the formula

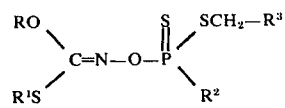

in which R is (1) alkyl or (2) allyl; $R^1$ is alkyl; $R^2$ is alkyl; and $R^3$ is (1) hydrogen, (2) lower alkylthio, (3) cyano, (4) phenylthio, (5) substituted phenylthio wherein the substituent is halogen, (6) ethynyl, or (7) $CCl_2=CH-$, their use as insecticides and acaricides, a process for preparing the compounds, intermediates having the formula

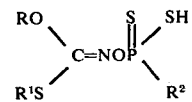

where R is alkyl or allyl, $R^1$ is alkyl and $R^2$ is alkyl and useful in preparing the above compounds and a process for preparing the intermediates.

1 Claim, No Drawings

CERTAIN THIOFORMALDOXIMINO DITHIOPHOSPHORIC ACIDS

This is a division of Application Ser. No. 26,149 filed Apr. 6, 1970, now U.S. Pat. No. 3,652,736.

This invention relates to certain novel chemical compounds, their use as insecticides and acaricides, a process for preparing the compounds, intermediates useful in preparing the compounds and a process for preparing the intermediates.

The compounds of this invention are those having the formula

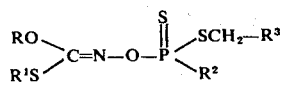

in which R is (1) alkyl having 1 to 4 carbon atoms, preferably branched chained, more preferably methyl and t-butyl or (2) allyl; $R^1$ is alkyl having 1 to 4 carbon atoms, preferably methyl; $R^2$ is alkyl having 1 to 4 carbon atoms, preferably 1 to 2 carbon atoms and $R^3$ is (1) hydrogen; (2) lower alkylthio having 1 to 4 carbon atoms; (3) cyano; (4) phenylthio; (5) substituted phenylthio wherein the substituent is halogen preferably, chlorine; (6) ethynyl, or (7) $CCl_2=CH-$.

The compounds of the present invention can be prepared according to the following reactions:

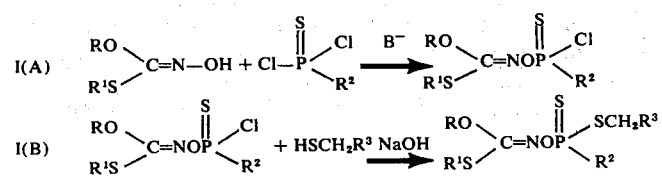

in which R, $R^1$, $R^2$, and $R^3$ are as defined.

In the event that the desired compound cannot be prepared because of difficulty of preparing or obtaining the compound $HSCH_2R^3$ of reaction I(B), then the following reaction can be utilized to obtain the compounds of this invention.

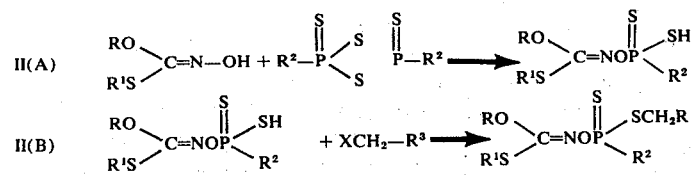

in which R, $R^1$, $R^2$, and $R^3$ are as defined and X is chlorine, bromine, or iodine.

The compound

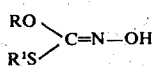

recited in reaction I(A) and I(B) were R and $R^1$ are as defined can be prepared according to the general procedure stated in Belgium Pat. No. 710,649 by reaction of the appropriate xanthate, with hydroxyl amine hydrochloride followed by reaction with the appropriate alkyl halide.

Preferably, reaction I(A) is carried out by reacting preferably equal mole amounts of the two reactants. If an excess of either reactant is used, the reaction still proceeds but yields are reduced. The reactants can be combined in any desired manner but preferably, the reaction is run in a solvent such as THF by first preparing the salt of the oxime reactant with an acid acceptor such as potassium t-butoxide at room temperature and then preferably, slowly adding the dichloride reactant thereto, preferably in solution with a solvent, for example, THF, at a temperature below about 15°C. for control. However, the oxime reactant can be used in place of the salt, preferably in the presence of the acid acceptor. The resulting produce is recovered and purified by standard procedure. For example, the resulting product can be recovered from the reaction mixture and purified from the reaction mixture by adding the mixture to a non-polar solvent such as benzene. The benzene mixture is then washed with water, dilute NaOH solution and then again by water. The benzene is evaporated after the water has been removed, for example, by treatment with anhydrous $MgSO_4$ to yield the purified product.

Reaction I(B) is carried out by reacting preferably equal mole amounts of the two reactants. If an excess of either reactant is used, the reaction still proceeds but yields are reduced. The reactants can be combined in any manner but preferably the phosphorus-containing reactant is slowly added to the reactant containing the —SH group in a solvent such as THF, preferably with stirring. More preferably, an alkali metal salt of this reactant is used to reduce the chance of a violent reaction. The temperature of the reaction is not critical, however, better yields are obtained by heating the reactants at reflux for a time sufficient to allow completion of the reaction. The resulting product can be recovered from the reaction mixture and purified by standard procedures. For example, the desired reaction product can be recovered from the reaction mixture by adding the mixture to a non-polar solvent such as benzene. The benzene mixture is then washed with water, dilute NaOH solution and then again by water. The benzene is evaporated after the water has been removed, for example, by treatment with anhydrous $MgSO_4$ to yield the purified product.

The process of this invention is represented by reaction II(A) and gives intermediate compounds useful to prepare the compounds of this invention. In other words, the process of this invention is a process for preparing a compound having the formula:

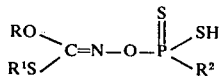

in which R, R¹, and R² are as defined comprising reacting a compound of the formula

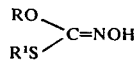

in which R and R¹ are as defined with a compound of the formula

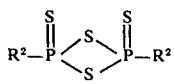

in which R² is as defined.

The process of this invention is carried out by merely reacting the two reactants. Preferably, about 2 moles of the oxime reactant per mole thionophosphine sulfide reactant should be used. If other proportions of either reactant are used, the reaction still proceeds but yields are lowered. The reactants can be combined in any desired manner. The reaction readily proceeds at room temperature and preferably is run under anhydrous conditions in a solvent such as benzene. The dithiophosphonic acid product can be recovered from its solvents in pure form, but it is preferred to not do so. If prolonged storage of the compound is desired, it is preferable to prepare either the alkali, alkaline, or heavy metal salt of the acid.

Another process of this invention is represented by reaction II(B) which utilizes as a reactant the product of reaction II(A) preferably as a solution in the solvent utilized for reaction II(A).

In this process, the reaction is carried out by reacting preferably about equal mole amounts of the reactants. If an excess of either reactant is used, the reaction still proceeds but again yields are lowered. Although the reactants can be combined in any desired manner, it is preferred to add the halide reactant to a solution of the dithiophosphonic acid reactant, preferably the acid is not recovered from the solvent in which it is prepared. Preferably, the reaction is carried out at below room temperature about 10° – 20°C. for control and in the presence of a base, such as triethyl amine, to take up the liberated acid halide reaction product. The reaction product is recovered by conventional means such as described for reaction I(B).

The novel intermediate compounds of this invention which are (1) useful in preparing the compounds of this invention, for example, by reaction II(B), heretofore described or (2) as insecticides or acaricides, are those having the formula:

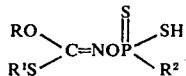

in which R is (1) alkyl having 1 to 8 carbon atoms, methyl or (2) lower alkylthiomethyl having 1 to 4 carbon atoms, preferably 1 to 2 carbon atoms; R¹ is alkyl having 1 to 4 carbon atoms, preferably methyl and R² is alkyl having 1 to 4 carbon atoms, preferably 1 to 2 carbon atoms.

These intermediate compounds are preparable according to reaction II(A) and the subsequent discussion thereof.

If desired, the alkali, alkaline earth or heavy metal salts of the intermediate acid compounds can be prepared by convention techniques such as by reacting the acid with a base. The salts will either be mono, di or tri basic depending upon the valency of the metal atom used to form the salt.

Preparation of the compounds of this invention, the process for preparing intermediates and the intermediates are illustrated by the following examples:

EXAMPLE I

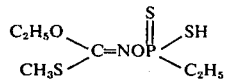

0-(0-ethyl-S-methylthioformaldoximino), ethyl-dithiophosphonic acid

This example teaches the synthesis of the oximino, ethyl phosphonic acid useful in the preparation of the compounds of this invention.

12.4 grams (0.05 moles) of ethylthionophosphine sulfide is combined with 200 ml. of anhydrous benzene in a 1000 ml. beaker. The mixture is magnetically stirred at room temperature, and 13.5 grams (0.1 mole) of 0-ethylmethylthioformaldoxime is added, and the resulting mixture is stirred for 30 minutes until a clear solution is obtained. The benzene is evaporated to yield the desired product. I.R. confirms the desired product.

EXAMPLE II

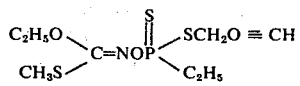

0-(0-ethyl,S-methylthioformaldoximino), ethyl-S-propargyl phosphonodithioate.

12.4 grams (0.05 mole) of ethylthiophosphine sulfide is combined with 200 ml. of anhydrous dioxane in a 1000 ml. beaker, and 13.5 gms. (0.1 mole) of 0-ethyl, methylthioformaldoxime is added. The mixture is stirred magnetically at room temperature until a clear solution containing the compound of Example I is obtained. The solution is cooled in an ice bath to 10°C., and 11.9 gms. (0.1 mole) of propargylbromide is added followed by 15.1 gms. (0.15 mole) of triethylamine added over a period of 10 minutes. The resulting mixture is stirred at room temperature for one hour, then poured into 300 ml. of benzene. The benzene mixture is washed with 200 ml. of H₂O, 100 ml. of saturated NaHCO₃, followed by 2 – 100 ml. portions of H₂O. The benzene phase is dried with anhydrous MgSO₄ and evaporated under reduced pressure to yield 27 gms. (90.3% of theory) of the desired compound. $N_D^{30}$=1.5643.

The following is a Table of certain selected compounds that are preparable according to the procedure described hereto. Compound numbers are assigned to

TABLE I

| COMPOUND NUMBER | R | R¹ | R² | R³ | | $N_D^{30}$ |
|---|---|---|---|---|---|---|
| 1[a] | $C_2H_5$ | $CH_3$ | $C_2H_5$ | —C | CH | 1.5693 |
| 2 | $C_2H_5$ | $CH_3$ | $C_2H_5$ | —C | N | 1.5618 |
| 3 | $C_2H_5$ | $CH_3$ | $C_2H_5$ | —CH=$CCl_2$ | | 1.5705 |
| 4 | $C_2H_5$ | $CH_3$ | $C_2H_5$ | —$SCH_2CH_3$ | | 1.5545 |
| 5 | $C_2H_5$ | $CH_3$ | $C_2H_5$ | —S—C₆H₄—Cl | | 1.5925 |
| 6 | $C_2H_5$ | $CH_3$ | $C_2H_5$ | H | | 1.5541 |
| 7 | $CH_2$=$CHCH_2$— | $CH_3$ | $C_2H_5$ | —C | N | 1.5838 |
| 8 | $CH_2$=$CHCH_2$— | $CH_3$ | $C_2H_5$ | —C | CH | 1.5827 |
| 9 | $CH_2$=$CHCH_2$— | $CH_3$ | $C_2H_5$ | —$SCH_3$ | | 1.5990 |
| 10 | $CH_2$=$CHCH_2$ | $CH_3$ | $C_2H_5$ | —$SCH_2CH_3$ | | 1.5937 |

[a]) Prepared in Example II

The following tests illustrate utility of the compounds as insecticides and acaricides.

INSECTICIDAL EVALUATION TESTS

The following insect species were used in evaluation tests for insecticidal activity:
1. Housefly (HF) - *Musca domestica* (Linn.)
2. German Roach (GR) - *Blatella germanica* (Linn.)
3. Salt-Marsh Caterpillar (SMC) - *Estigmene acrea* (Drury)
4. Lygus Bug (LB) - *Lygus hesperus* (Knight)
5. Bean Aphid (BA) - *Aphis fabae* (Scop.)

The Housefly (HF) was used in evaluation tests of selected compounds as insecticides by the following procedure. A stock solution containing 100 ug/ml. of the toxicant in an appropriate solvent was prepared. Aliquots of this solution were combined with 1 milliliter of an acetone-peanut oil solution in an aluminum dish and allowed to dry. The aliquots were there to achieve desired toxicant concentration ranging from 100 ug. per dish to that at which 50% mortality was attained. The dishes were placed in a circular cardboard cage, closed on the bottom with cellophane and covered on top with cloth netting. Twentyfive female houseflies, three to five days old, were introduced into the cage and the percent mortality was recorded after 48 hours. The LD-50 values are expressed in terms of ug. per 25 female flies. The results of these insecticidal evaluation tests are given in Table II under "HF".

In the German Cockroach (GR) tests, 10 one-month old nymphs were placed in separate circular cardboard cages sealed on one end with cellophane and covered by a cloth netting on the other. Aliquots of the toxicants, dissolved in an appropriate solvent, were diluted in water containing 0.002% of a wetting agent, Sponto 221, - (a polyoxyether of alkylated phenols blended with organic sulfonates). Test concentrations ranged from 0.1% downward to that at which 50% mortality was obtained. Each of the aqueous suspensions of the candidate compounds was sprayed onto the insects through the cloth netting by means of a hand-spray gun. Percent mortality in each case was recorded after 72 hours, and the LD-50 values, expressed as percent of toxicant in the aqueous spray, were recorded. These values are reported under the column "GR" in Table II.

For testing the Salt-Marsh Caterpillar, test solutions were prepared in an identical manner and at concentrations the same as for the German Cockroach above. Sections of bitter dock, *Rumex obtusifolus*, leaves, 1–1.5 inches in length were immersed in the test solutions for 10 to 15 seconds and placed on a wire screen to dry. The dried leaf was placed on a moistened piece of filter paper in a Petri dish and infested with 5 – 3rd Instar larvae. Mortality of the larvae was recorded after 72 hours and the LD-50 values are expressed as percent active ingredient in the aqueous suspension.

The Lygus Bug (LB), *Lygus hesperus*, was tested similarly as the German Cockroach. The caged insects were sprayed with the candidate compounds at concentrations ranging from 0.05% downward to that at which 50% mortality was obtained. After twenty-four and seventy-two hours, counts were made to determine living and dead insects. The LD-50 (Percent) values were calculated. These values are reported under the Column "LB" in Table II.

The insect species black bean aphid (BA), *Aphis fabae* (Scop), was also employed in the test for insecticidal activity. Young nasturtium, (*Tropaeolum* sp.), plants, approximately 2 to 3 inches tall, were used as the host plants for the bean aphid. The host plant was infested with approximately 50 – 75 of the aphids. The test chemical was dissolved in acetone, added to water which contained a small amount of Sponto 221, an emulsifying agent. The solution was applied as a spray to the infested plants. Concentrations ranged from 0.05 percent downward until an $LD_{50}$ value was achieved. These results are given in Table II under Column "BA".

ACARICIDAL EVALUATION TEST

The two-spotted mite (2SM), *Tetranychus urticae* (Koch), was employed in tests for miticides. Young pinto bean plants or lima bean plants (*Phaseolus sp.*) in the primary leaf stage were used as the host plants. The young pinto bean plants were infested with about 100 mites of various ages. Dispersions of candidate materials were prepared by dissolving 0.1 gram in 10 ml. of a suitable solvent, usually acetone. Aliquots of the toxicant solutions were suspended in water containing 0.002% v/v Sponto, polyoxyethylene ether sorbitan monolaurate, an emulsifying agent, the amount of water being sufficient to give concentrations of active ingredient ranging from 0.05% to that at which 50% mortality was obtained. The test suspensions were then sprayed on the infested plants to the point of run off. After seven days, mortalities of post-embryonic and ovicidal forms were determined. The percentage of kill was determined by comparison with control plants which had not been sprayed with the candidate compounds. The LD-50 values were calculated using well-known procedures. These values are reported under the columns "2SM-PE" and "2SM-Eggs" in Table II.

SYSTEMIC EVALUATION TEST

This test evaluates the root absorption and upward translocation of the candidate systemic compound. The two-spotted mite (2SM), Tetranychus urticae (Koch.) and the Bean Aphid (BA), Aphis fabae (Scop.), were employed in the test for systemic activity.

Young pinto bean plants in the primary leaf stage were used as host plants for the two-spotted mite. The pinto bean plants were placed in bottles containing 200 ml. of the test solution and held in place with cotton plugs. Only the roots were immersed. The test solutions were prepared by dissolving the compounds to be tested in a suitable solvent, usually acetone, and then diluting with distilled water. The final acetone concentration never exceeded about 1 percent. The toxicants were initially tested at a concentration of 10 parts per million (p.p.m.). Immediately after the host plant was placed in the test solution, it was infested with the test species. Mortalities were determined after seven days.

Young nasturtium plants were used as the host plants for the Bean Aphid. The host plants were transplanted into one pound of soil that had been treated with the candidate compound. Immediately after planting in the treated soil, the plants were infested with the aphids. Concentrations of toxicant in the soil ranged from 10 p.p.m. per pound of soil downward until an LD-50 value was obtained. Mortality was recorded after 72 hours.

The percentage of kill of each test species was determined by comparison with control plants placed in distilled water or untreated soil. The LD-50 values were calculated. These systemic test results are reported in Table II under the columns "BA-Sys" and "2SM-Sys".

As those in the art are well aware, various techniques are available for incorporating the active component or toxicant in suitable pesticidal compositions, thus, the pesticidal compositions can be conveniently prepared in the form of liquids or solids, the latter preferably as homogeneous free-flowing dust commonly formulated by admixing the active component with finely divided solids or carriers as exemplified by talc, natural clays, diatomaceous earth, various flours such as walnut shell, wheat, soya bean, cottonseed and so forth.

Liquid compositions are also useful and normally comprise a dispersion of the toxicant in a liquid media, although it may be convenient to dissolve the toxicant directly in a solvent such as kerosene, fuel oil, xylene, alkylated naphthalenes or the like and use such organic solutions directly. However, the more common procedure is to employ dispersions of the toxicant in an aqueous media and such compositions may be produced by forming a concentrated solution of the toxicant in a suitable organic solvent followed by dispersion in water, usually with the aid of surface active agents. The latter, which may be the anionic, cationic, or nonionic types, are exemplified by sodium stearate, potassium oleate and other alkaline metal soaps and detergents such as sodium lauryl sulfate, sodium naphthalene sulfonate, sodium alkyl naphthalane, sulfonate melhyl cellulose, fatty alcohol ethers, polyglycol fatty acid esters and other polyoxyethylene surface active agents. The proportion of these agents commonly comprises 1 – 15% by weight of the pesticidal compositions although the proportion is not critical and may be varied to suit any particular situation.

I claim:

1. The compound having the formula

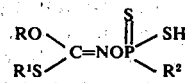

in which R is (1) alkyl having 1 to 4 carbon atoms; or (2) allyl, $R^1$ is alkyl having 1 to 4 carbon atoms; and $R^2$ is alkyl having 1 to 4 carbon atoms.

* * * * *

TABLE II

| COMPOUND NUMBER | HF ug | GR % | LB % | LD$_{50}$ Values SMC % | BA % | BA-SYS p.p.m. | PE % | EGGS % | SYS p.p.m. |
|---|---|---|---|---|---|---|---|---|---|
| 1 | 10 | .01 | .003 | .03 | .0008 | >10.0 | .01 | >.05 | >1 |
| 2 | 30 | .03 | .003 | >.1 | .003 | >10.0 | .003 | .03 | >1 |
| 3 | 30 | >.1 | >.05 | .05 | .005 | >10.0 | .03 | >.05 | >1 |
| 4 | 30 | .05 | .001 | >.1 | .0005 | >10.0 | .03 | .03 | >1 |
| 5 | 100 | >.1 | >.05 | >.1 | .05 | >10.0 | >.05 | >.05 | |
| 6 | 30 | .05 | .008 | | .003 | 8.0 | >.05 | >.05 | |
| 7 | 35 | >.1 | .003 | >.1 | .003 | >10.0 | .003 | >.05 | 8 |
| 8 | 30 | .1 | .03 | .05 | .003 | >10.0 | .03 | >.05 | >10 |
| 9 | >100 | >.1 | .01 | >1 | .003 | >10.0 | .008 | >.05 | 8 |
| 10 | 80 | >.1 | .008 | >1 | .003 | >10.0 | .008 | >.05 | >10 |